United States Patent [19]
Jaedicke et al.

[11] 4,100,197
[45] Jul. 11, 1978

[54] MANUFACTURE OF ECHINENONE

[75] Inventors: Hagen Jaedicke, Ludwigshafen; Joachim Paust, Neuhofen; Joachim Schneider, Ludwigshafen, all of Fed. Rep. of Germany

[73] Assignee: BASF Aktiengesellschaft, Ludwigshafen am Rhein, Fed. Rep. of Germany

[21] Appl. No.: 705,281

[22] Filed: Jul. 14, 1976

[30] Foreign Application Priority Data

Aug. 5, 1975 [DE] Fed. Rep. of Germany ....... 2534807

[51] Int. Cl.$^2$ ............................................. C07C 45/02
[52] U.S. Cl. ................................................ 260/586 P
[58] Field of Search ....................... 260/586 P, 586 D

[56] References Cited

U.S. PATENT DOCUMENTS

| | | | |
|---|---|---|---|
| 2,870,197 | 1/1959 | Isler et al. | 260/586 P |
| 2,871,267 | 1/1959 | Petracek et al. | 260/586 P |
| 3,646,149 | 2/1972 | Morel | 260/586 P |
| 3,790,635 | 2/1974 | Morel | 260/586 P |

OTHER PUBLICATIONS

Petrachek et al., J.A.C.S., vol. 78, pp. 1427–1433 (1956).
Sidgwick, The Chemical Elements & Their Compounds, vol. II, pp. 1225–1239 (1952).

*Primary Examiner*—James O. Thomas, Jr.
*Assistant Examiner*—James H. Reamer
*Attorney, Agent, or Firm*—Keil, Thompson & Shurtleff

[57] ABSTRACT

Echinenone is produced by oxidizing β-carotene or retro-dehyro-carotene with iodic acid or a salt of iodic acid in the presence of a catalyst and of an inert diluent or solvent.

6 Claims, No Drawings

MANUFACTURE OF ECHINENONE

The present invention relates to a process for the manufacture of echinenone by oxidizing β-carotene or retro-dehydro-carotene.

The natural carotinoid echinenone, as provitamin A, is a particularly suitable additive for animal feeds and a food dye.

The manufacture of echinenone from β-carotene by reaction with N-bromosuccinimide has been disclosed. In this reaction, impure echinenone is obtained in low yields as a by-product (J. Am. Chem. Soc. 78 (1956), 1,427). It has also been disclosed that the direct oxidation of β-carotene with sodium metaperiodate leads canthaxanthin, a carotinoid which is oxygenated on both sides (German pat. No. 1,793,308).

We have now found a process for the manufacture of echinenone by oxidating β-carotene or retro-dehydro-carotene, wherein the oxidation is carried out with iodic acid or a salt of iodic acid in the presence of the halogens chlorine, bromine or iodine or of the oxides or oxo-acids of selenium or of elements of groups Va, VIa or VIIa of the periodic table, or salts of these oxo-acids, or of the oxides of the elements of group VIII of the periodic table as a catalyst, and in the presence of an inert diluent or solvent, at from 0° to 50° C.

Essential advantages of the process according to the invention are its simplicity, the good yield and the high purity in which the echinenone is obtained.

The starting materials are used for example in the form of dilute solutions for the oxidation. Advantageously, solutions containing from 1 to 10 g of starting material per liter of an inert, readily volatile, water-immiscible solvent are used.

Suitable diluents or solvents are chlorinated aliphatic hydrocarbons, e.g. chloroform, methylene chloride, 1,1-dichloroethane, 1,2-dichloroethane, 1,1,2-trichloroethane, 1,1,2,2-tetrachloroethane, 1,2-dichloroethylene and 1,1,2-trichloroethylene, aromatic hydrocarbons, e.g. benzene, toluene, nitrobenzene or chlorobenzene, dialkyl ethers, e.g. diethyl ether and di-n-propyl ether, or carbon disulfide. Chloroform, methylene chloride and nitrobenzene are particularly suitable solvents. Mixtures of these diluents or solvents can also be used.

Suitable oxidizing agents are salts of iodic acid, especially the alkaline earth metal salts, alkali metal salts or ammonium salts, or the free acid. They are advantageously added to the reaction mixture in the form of an aqueous solution of from 5 to 50 percent strength by weight. The molar ratio of oxidizing agent to starting material is advantageously from 1:1 to 100:1 and preferably from 1:1 to 20:1. Using a more than 100-fold molar excess of oxidizing agent has no effect on the reaction.

The oxidation is catalyzed by the halogens chlorine, bromine or iodine, or by oxides or oxo-acids of selenium or of the elements of groups Va, VIa or VIIa of the periodic table or by salts of these oxo-acids or by oxides of the elements of group VIII of the periodic table. Examples of suitable catalysts are selenium dioxide, selenous acid and its salts, selenic acid and its salts, vanadium pentoxide, vanadates, polyvanadic acids and their salts, heteropolyacids of vanadium, especially with the elements tungsten, molybdenum and phosphorus, and their salts, molybdenum trioxide, molybdates, especially ammonium molybdate, polymolybdates, heteropolyacids of molybdenum, especially with the elements vanadium or phosphorus, tungsten trioxide, tungstates, polytungstic acids and their salts, heteropolyacids of tungsten, especially with the elements vanadium and phosphorus, and their salts, manganese dioxide, nickel oxide and osmium tetroxide.

Bromine, iodine and osmium tetroxide are preferred catalysts; iodine is a particularly suitable catalyst.

The catalyst is added in the pure form or in solution, e.g. in the solvent which has been used to dissolve the starting material, or in water. The catalyst can also be formed in situ. The amount of catalyst is advantageously from 0.1 to 10 percent by weight, preferably from 1 to 5 percent by weight, based on starting material.

Because of the sensitivity of the compounds to heat, the oxidation is carried out at low temperatures; suitable temperatures are from 0° to 50° C, preferably from 15° to 30° C. The reaction takes place in a pH range extending from strongly acid values to pH 13. A pH of from 2 to 6 is preferred. Acids, e.g. sulfuric acid, hydrochloric acid or acetic acid, or buffer mixtures, are used to bring the pH to the desired value.

The reaction time is from 1 to 250 hours depending on the conditions chosen. In an advantageous embodiment, less than 100 hours are required to obtain an optimum yield of echinenone.

To prevent undesirable oxidation of the compounds by atmospheric oxygen, the reaction is preferably carried out under an inert gas atmosphere. Inert gases suitable for use under the reaction conditions are argon, neon, helium, carbon dioxide and especially nitrogen.

In a preferred embodiment of the process, an aqueous solution of the oxidizing agent is added to a solution of the starting material in a water-immiscible diluent or solvent, which is inert under the reaction conditions, under an inert gas atmosphere. The aqueous phase is then brought to the desired pH by means of an acid or a buffer mixture. After adding the catalyst, the reaction mixture is stirred for some time. The organic phase is then separated off, washed, dried and concentrated. The echinenone can then be precipitated with polar solvents, such as alcohols, e.g. methanol or ethanol. Alternatively, the echinenone can be precipitated directly from the reaction mixture by adding methanol or ethanol. After working up, the product is advantageously subjected to an isomerization.

EXAMPLE 1

10 g of β-carotene are dissolved in 1 liter of chloroform and a solution of 8 g of sodium iodate in 100 ml of water is added. 200 mg of iodine are then added and the mixture is stirred for 60 hours at room temperature under a nitrogen atmosphere. It is then washed with three 500 ml portions of water, the organic phase is concentrated to dryness under reduced pressure and 300 ml of methanol are added to the residue. After stirring for 2 hours at 0° C, 9.8 g of fine crystals of echinenone, $E_{1\ cm}^{1\%} = 1,410$ at $\lambda_{max} = 464$ nm in cyclohexane, are obtained.

EXAMPLE 2

1 g of β-carotene is dissolved in 100 ml of chloroform. An aqueous solution of 0.9 g of ammonium iodate in 1 ml of water is added, followed by dropwise addition of a solution of 15 mg of bromine in 20 ml of chloroform. The mixture is stirred for 96 hours at room temperature and 100 ml of water are added. The phases are then separated and the organic solution is washed with 200 ml of water, then with 100 ml of normal sodium thiosulfate solution, and again with 100 ml of water. It is dried over sodium sulfate and filtered, and the solvent is distilled off under reduced pressure. 200 ml of methanol are added to the residue, and the mixture is heated at the reflux temperature for one minute and then rapidly cooled to −20° C. It is then stirred for 4 hours, after which 0.96 g of fine crystals of echinenone are filtered off; $E_{1\ cm}^{1\%} = 1,640$ at $\lambda_{max} = 462$ nm in cyclohexane.

We claim:

1. A process for the manufacture of echinone by oxidizing β-carotene or retro-dehydro-carotene, wherein the oxidation is carried out with iodic acid or a salt of iodic acid in a proportion of 1 to 20 moles per mole of β-carotene or retro-dehydro-carotene in the presence of the halogens bromine or iodine as a catalyst, and in the presence of an inert diluent or solvent, at from 0° to 50° C.

2. A process as claimed in claim 1, wherein the oxidation is carried out with the ammonium salt of iodic acid.

3. A process as claimed in claim 1, wherein the oxidation is carried out with the alkali metal salt of iodic acid.

4. A process as claimed in claim 1, wherein the oxidation is carried out in a chlorinated aliphatic hydrocarbon serving as the diluent or solvent.

5. A process as claimed in claim 1, wherein the amount of bromine or iodine catalyst is in the range of 0.1 to 10% by weight, based on the β-carotene or retro-dehydro-carotene.

6. A process as claimed in claim 1, wherein the amount of bromine or iodine catalyst is in the range of 1 to 5% by weight, based on the β-carotene or retro-dehydro-carotene.

* * * * *

UNITED STATES PATENT AND TRADEMARK OFFICE
CERTIFICATE OF CORRECTION

PATENT NO. : 4,100,197
DATED : July 11, 1978
INVENTOR(S) : JAEDICKE ET AL

It is certified that error appears in the above-identified patent and that said Letters Patent are hereby corrected as shown below:

Claim 1, line 1, cancel "echinone" and substitute --echinenone--.

Signed and Sealed this

Fifteenth Day of May 1979

[SEAL]

Attest:

RUTH C. MASON
Attesting Officer

DONALD W. BANNER
Commissioner of Patents and Trademarks